(12) United States Patent
Meder et al.

(10) Patent No.: US 9,237,999 B2
(45) Date of Patent: Jan. 19, 2016

(54) COSMETIC OR PHARMACEUTICAL COMPOSITION COMPRISING MODIFIED POLYORGANOSILOXANES

(71) Applicant: Clariant Produkte (Deutschland) GmbH, Sulzbach (DE)

(72) Inventors: Markus Meder, Markt Schwaben (DE); Peter Klug, Grossostheim (DE); Torsten Henning, Hanau (DE); Waltraud Simsch, Kelkheim (DE); Sabine Haala, Hanau (DE); Carsten Mueller, Frankfurt am Main (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 0 days.

(21) Appl. No.: 13/933,847

(22) Filed: Jul. 2, 2013

(65) Prior Publication Data
US 2013/0344021 A1    Dec. 26, 2013

Related U.S. Application Data

(62) Division of application No. 11/082,448, filed on Mar. 17, 2005, now abandoned.

(30) Foreign Application Priority Data

Mar. 20, 2004    (DE) .......................... 10 2004 013 795

(51) Int. Cl.
| | |
|---|---|
| A61Q 5/02 | (2006.01) |
| A61K 8/00 | (2006.01) |
| A61K 8/18 | (2006.01) |
| A61Q 5/00 | (2006.01) |
| A61Q 9/00 | (2006.01) |
| A61K 8/898 | (2006.01) |
| A61Q 5/12 | (2006.01) |
| A61Q 5/06 | (2006.01) |
| A61Q 19/10 | (2006.01) |

(52) U.S. Cl.
CPC . *A61K 8/898* (2013.01); *A61Q 5/00* (2013.01); *A61Q 5/004* (2013.01); *A61Q 5/12* (2013.01); *A61Q 5/06* (2013.01); *A61Q 19/10* (2013.01)

(58) Field of Classification Search
CPC ............ A61Q 5/12; A61Q 5/004; A61Q 5/00
See application file for complete search history.

(56) References Cited

U.S. PATENT DOCUMENTS

| | | | |
|---|---|---|---|
| 4,533,714 A | 8/1985 | Sebag et al. | |
| 4,587,321 A | 5/1986 | Sebag et al. | |
| 4,680,366 A | 7/1987 | Tanaka et al. | |
| 4,833,225 A | 5/1989 | Schaefer et al. | |
| 4,891,166 A | 1/1990 | Schaefer et al. | |
| 5,025,076 A | 6/1991 | Tanaka et al. | |
| 5,075,403 A | 12/1991 | Kirk | |
| 6,132,739 A | 10/2000 | Leverett | |
| 6,352,699 B1* | 3/2002 | Mondet et al. | ................ 424/401 |
| 2003/0198607 A1* | 10/2003 | Chaudhuri | ...................... 424/59 |
| 2004/0236055 A1 | 11/2004 | Danner | |
| 2005/0169878 A1 | 8/2005 | Elder et al. | |
| 2007/0041930 A1 | 2/2007 | Meder et al. | |
| 2008/0014166 A1 | 1/2008 | Klug et al. | |

FOREIGN PATENT DOCUMENTS

| | | |
|---|---|---|
| DE | 198 17 776 | 10/1999 |
| EP | 1512391 | 3/2005 |
| WO | WO 02/092666 | * 11/2002 |
| WO | WO 02/092666 | 11/2004 |
| WO | WO 2005/035628 | 4/2005 |

OTHER PUBLICATIONS

English Language Abstract of JP 11012152, Jan. 19, 1999.
English Language Abstract of JP 09194335, Jul. 29, 1997.
English Language Abstract of DE 198 17 776, Oct. 28, 1999.
"Keshouhinn handbook" (Cosmetic Handbook), Nikko Chemicals Co., Ltd., Nov. 1, 1996, p. 82.
Fragrance Journal, 2004, vol. 32, No. 2, pp. 89-90.
"Development and future problem of silicone as a raw material for staying mousses", Asao Harashima, Fragrance Journal, 1985, No. 70, pp. 112-115.
"Application of new ingredients in hair care products", Kiyoshi Inoue, Fragrance Journal, 1999, vol. 27, No. 1, pp. 119-126.

* cited by examiner

*Primary Examiner* — Johann R Richter
*Assistant Examiner* — Genevieve S Alley
(74) *Attorney, Agent, or Firm* — Tod A. Waldrop

(57) ABSTRACT

Cosmetic or pharmaceutical compositions comprising one or more substituted aminopolyorganosiloxanes ($S_H$) with substituted amino groups which are bonded to silicon atoms of the polysiloxane basic structure via alkylene bridges or mono- or oligo(alkylenamino)alkylene bridges, where the amino groups present in the aminopolyorganosiloxanes ($S_H$) are substituted at least partially by a radical of the formula ($\epsilon$)

$$T-CH_2-CHOH-CH_2- \qquad (\epsilon),$$

in which T is the radical of a surfactant monoalcohol polyglycol ether with emulsifier character, the amino groups present in the aminopolyorganosiloxanes ($S_H$) are substituted in the average ratio of at least 1.5 radicals of the formula ($\epsilon$) per Si-bonded aminoalkyl group or amino-mono- or -oligo-(alkylenamino)-alkyl group, and present amino groups are, if appropriate, acylated and/or alkylated and/or benzylated and/or protonated at least partially to give amide groups, are described.

8 Claims, No Drawings

COSMETIC OR PHARMACEUTICAL COMPOSITION COMPRISING MODIFIED POLYORGANOSILOXANES

The invention relates to cosmetic or pharmaceutical compositions comprising aminopolyorganosiloxanes which are substituted by alkyl polyglycol ether groups.

It is known that aminosiloxanes with primary and secondary nitrogen groups and sometimes present reactive silanol groups are incorporated into hair shampoo formulations as conditioning agents. These products are not water-soluble and can only be incorporated in the presence of interface-active substances. In order to improve the solubility in water, the aminosiloxanes can additionally be substituted by polyoxyalkylene groups, as described in U.S. Pat. No. 5,075,403. It is disadvantageous that these have high viscosity and can only be handled in dilution, during use remain for the greatest part in the aqueous phase and do not attach to the hair in the desired manner. WO 02/092666 claims aminopolyorganosiloxanes and their use for the softening finishing of textile fiber materials.

The object of the present invention was to prepare compositions for cosmetic or pharmaceutical products which are water-soluble, emulsifiable, compatible with additives and auxiliaries customary in cosmetic compositions, can be incorporated easily into formulations, produce the clearest possible appearance and exhibit a softening effect. Moreover, the compositions are to have good substantivity and bring about an improvement in the color absorption behavior and an increase in the color stability and shape retention for tinted or colored hair.

Surprisingly, it has been found that substituted aminopolyorganosiloxanes ($S_H$) comprising substituted amino groups which are bonded to the silicon atoms of the polysiloxane basic structure via alkylene bridges or mono- or oligo(alkylenamino)-alkylene bridges, in which the amino groups present in the aminopolyorganosiloxanes are substituted at least partially by a radical of the formula (ε), $$T\text{-}CH_2\text{—}CHOH\text{—}CH_2\text{—} \qquad (\epsilon),$$

in which T is the radical of a surfactant monoalcohol polyglycol ether with emulsifier character, in the average ratio of at least 1.5 radicals of the formula (ε) per Si-bonded amino group or amino-mono- or -oligo(alkylenamino)alkyl group, and present amino groups are, if appropriate, acylated and/or alkylated and/or benzylated and/or protonated at least partially to give amide groups, exhibit excellent substantivity, and good conditioning and color-retaining to color-intensifying effects, in particular toward hair.

The present invention therefore provides cosmetic or pharmaceutical compositions, in particular for the care of the hair and of the skin, comprising one or more substituted aminopolyorganosiloxanes ($S_H$) with substituted amino groups which are bonded to silicon atoms of the polysiloxane basic structure via alkylene bridges or mono- or oligo(alkylenamino) alkylene bridges, where the amino groups present in the aminopolyorganosiloxanes ($S_H$) are substituted at least partially by a radical of the formula (ε)

$$T\text{-}CH_2\text{—}CHOH\text{—}CH_2\text{—} \qquad (\epsilon),$$

in which T is the radical of a surfactant monoalcohol polyglycol ether with emulsifier character, the amino groups present in the aminopolyorganosiloxanes ($S_H$) are substituted in the average ratio of at least 1.5 radicals of the formula (ε) per Si-bonded aminoalkyl group or amino-mono- or -oligo-(alkylenamino)-alkyl group, and present amino groups are, optionally, at least partially, acylated to give amide groups and/or alkylated and/or benzylated and/or protonated.

The color absorption behavior of hair colorants can be improved by aminopolyorganosiloxanes ($S_H$). In hairstyling compositions, a volumizing and shine-imparting effect of the aminopolyorganosiloxanes ($S_H$) is also significant. Furthermore, the good solubility in water, but also the good compatibility with hydrophobic components, good dissolving, dispersing and emulsifying power, the favorable viscosity behavior coupled with low viscosity and good incorporability in highly concentrated form, and a clear appearance of the aminopolyorganosiloxanes ($S_H$) used according to the invention is advantageous. Aminopolyorganosiloxanes ($S_H$) are characterized by good skin sensory properties and exhibit good spreadability, and an excellent gliding and carrier effect. Moreover, they are insensitive toward heat, UV radiation and IR radiation. They are thus valuable constituents of haircare and hair-cleansing compositions, hair colorants, skincare and skin-cleansing compositions, sunscreen compositions, deodorants, antiperspirants and decorative cosmetics.

The compositions according to the invention may, for example, be aqueous, aqueous-alcoholic, aqueous-surface-active or alcoholic compositions, or compositions based on oil, inclusive compositions based on oil in anhydrous form, or emulsions, suspensions or dispersions.

In a preferred embodiment of the invention, the cosmetic or pharmaceutical compositions are in aqueous, aqueous-alcoholic, alcoholic or aqueous-surface-active form or represent compositions based on oil, in particular anhydrous compositions based on oil, or are in the form of emulsion, suspension or dispersion and, more particularly, in the form of fluids, foams, sprays, gels, mousse, lotions, creams or powders.

Using the aminopolyorganosiloxanes ($S_H$) it is possible to prepare clear, viscous, aqueous, aqueous-alcoholic, aqueous-surface-active compositions, alcoholic compositions and also compositions based on oil with a very esthetic appearance.

In a further preferred embodiment of the invention, the cosmetic or pharmaceutical compositions are cosmetic or pharmaceutical formulations.

The substituted aminopolyorganosiloxanes ($S_H$) used in the cosmetic and pharmaceutical compositions according to the invention can be prepared as described in WO 02/092666 by introducing the radicals (ε) and optionally one or more of the other substituents into corresponding starting aminopolyorganosiloxanes (S) which comprise primary and/or secondary amino groups which are bonded to silicon atoms of the polysiloxane basic structure via alkylene bridges or mono- or oligo(alkylenamino)alkyl bridges. In the process, the starting aminopolyorganosiloxanes (S) are reacted with at least one alcohol polyglycol ether monoglycidyl ether (H) and optionally subsequently acylated and/or alkylated and/or benzylated and/or protonated.

The alcohol polyglycol ether monoglycidyl ethers (H) are generally glycidyl ethers of alcohol polyglycol ethers and can be synthesized by the following formula

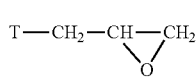
(I)

in which T is the radical of the corresponding surfactant alcohol polyglycol ether T-H, in particular as can be prepared by glycidyl ether formation of a corresponding surfactant alcohol polyglycol ether T-H.

The surface-active alcohol polyglycol ethers T-H may be any corresponding surfactants, e.g. in which the alcohol radical originates from an aromatic, alkylaromatic or preferably aliphatic alcohol having at least 8 carbon atoms, preferably having 8 to 24 carbon atoms, and the polyglycol radical is a polyalkylene glycol radical in which alkylene comprises 2 to 4 carbon atoms and at least some of the alkylene glycol units are ethylene glycol units. They advantageously have predominantly hydrophilic character and are preferably those in which the number of ethylenoxy units constitutes on average at least half of the alkylenoxy units present in T-H. Preferably, the alcohol polyglycol ethers T-H are those of the following average formula

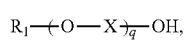 (II)

in which
$R_1$ is a hydrocarbon radical having 8 to 24 carbon atoms,
X is $C_{2-4}$-alkylene
and
q is 4 to 50,
where at least 50% of the q alkylene groups have the meaning of X.

The hydrocarbon radicals $R_1$ may be any radicals as otherwise customarily exist in nonionogenic surfactants. They are advantageously alkylaromatic or aliphatic and comprise advantageously 8 to 22, preferably 9 to 18, particularly preferably 11 to 16, carbon atoms.

If $R_1$ is aliphatic, it is preferably saturated; $R_1O$— in this case is preferably the radical of a primary, saturated, aliphatic alcohol or of a primary alkanol which advantageously comprises 9 to 18, preferably 11 to 16, carbon atoms. The corresponding aliphatic alcohol $R_1OH$ may be a linear fatty alcohol, e.g. lauryl alcohol, myristyl alcohol, cetyl alcohol, stearyl alcohol or behenyl alcohol or else a synthetic alcohol (e.g. from the oxo synthesis or from the Ziegler synthesis), which may be linear or branched, e.g. nonanol, isononanol, decanol, isodecanol, undecanol, tridecanol, isotridecanol or isohexadecanol.

The number q of the alkylenoxy units positioned on this alcohol to form the alcohol polyglycol ether, in particular of the formula II, is advantageously in the range from 4 to 30, preferably 4 to 20. 80% of the q alkylenoxy units are advantageously ethylenoxy units, and preferably 100% of the alkylenoxy units are ethylenoxy units.

The number of ethylenoxy units in T-H is advantageously 4 to 30, preferably 4 to 18, particularly preferably 5 to 12.

The surfactants T-H, in particular of the formula (II) are advantageously those whose HLB is greater than 7, and is advantageously in the range from 7 to 17, preferably 8 to 16.5, particularly preferably 9 to 16.

The primary and/or secondary amino groups in the aminopolysiloxanes (S) to be reacted with (H) are in particular part of the Si-bonded aminoalky groups or amino-mono- or -oligo(alkylenamino)alkyl groups and may be those as customarily exist in otherwise further unmodified aminopolysiloxanes and can form by using corresponding monomers in the preparation of the particular aminopolysiloxanes. Their alkyl and alkylene groups are advantageously those with 2 to 4 carbon atoms and may be linear or, if they contain 3 or 4 carbon atoms, also branched. Preferably, the aminoalkyl groups bonded to Si comprise 3 or 4 carbon atoms in the alkyl radical; the alkylene groups joining two amino groups preferably comprise 2 or 3 carbon atoms. Predominantly, the primary amino groups and the optionally present secondary amino groups in (S) are constituents of aminoalkyl groups or amino-mono- or -oligo(alkylenamino)alkyl groups of the formula

 (α)

in which
$Y_1$ is 1, 2 or 1,3-propylene or 2-methyl-1,3-propylene,
$Y_2$ is ethylene or propylene
and
p is 0, 1 or 2
bonded to silicon atoms of the polysiloxane basic structure.

$Y_1$ is advantageously 2-methyl-1,3-propylene or preferably 1,3-propylene; $Y_2$ is in particular 1, 2 or 1,3-propylene or is preferably ethylene; p is advantageously 0 or 1, preferably 1.

Preferably, the radicals of the formula (α) are those of the formula

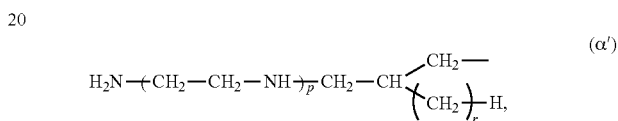 (α')

in which r is 0 or 1,
particularly preferably of the formula

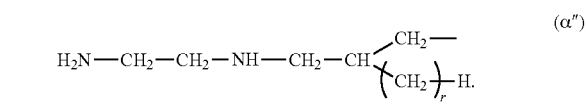 (α")

The index r is particularly preferably 0.

As a result of the reaction with (H), the particular radicals (ε) or

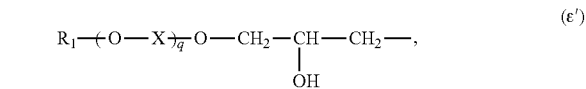 (ε')

are introduced into the aminoalkyl groups or amino-mono- or -oligo(alkylenamino)alkyl groups, in particular into those of the formula (α). In the process, the primary amino group reacts first, so that a first radical (ε) replaces a hydrogen atom of the primary amino group, and further radicals (ε) replace hydrogen atoms of the present secondary amino groups in random distribution. If desired, still acylatable amino groups can be acylated and/or any alkylatable amino groups present are alkylated and/or benzylated.

As a result of the acylation, preferably low molecular weight acyl radicals are introduced, advantageously those having 2 to 4 carbon atoms, e.g. acetyl, propionyl or butyryl, of which acetyl is particularly preferred. As a result of the alkylation and/or benzylation, likewise preferably low molecular weight alkyl radicals can be introduced, advantageously alkyl radicals with 1-4 carbon atoms, preferably ethyl or methyl, or benzyl radicals.

The reaction of (S) with (H) is advantageously carried out by reacting virtually all of the primary amino groups of (S) with (H) such that they are at least monosubstituted. Of the secondary amino groups which then remain, at least enough hydrogen atoms are replaced by a radical (ε) for the required degree of substitution of, on average, at least 1.5, primarily at least 1.8, preferably at least 2, radicals of the formula (ε) per Si-bonded aminoalkyl group or amino-mono- or -oligo(alkylenamino)alkyl group to be achieved. The fraction of secondary amino groups which are reacted with (H) can vary depending on the number of secondary amino groups in this Si-bonded group, in particular according to the meaning of p in the radical of the formula (α) or (α'). If p=0, this fraction is in particular at least half, or 50 to 100%, of the secondary amino groups, advantageously 80 to 100%, preferably 95 to 100% thereof; if p=1, at least one quarter, in particular 25 to 100% of the secondary amino groups, advantageously 50 to 100%, preferably 80 to 100% thereof; if p=2, at least one sixth, in particular 16.7 to 100% of the secondary amino groups, advantageously 40 to 100%, preferably 60 to 100% thereof.

The reaction of (S) with (H) can be carried out, for example if p is ≥1 advantageously up to a degree of substitution in the range from 40 to 100%, preferably 45 to 100%, particularly 50 to 100%, if p=0 advantageously up to a degree of substitution in the range from 75 to 100%, preferably 80 to 100%, particularly 90 to 100% [based on the reactive hydrogen atoms of the basic amino groups in (5)].

In a further preferred embodiment of the invention, the substituted aminopolyorganosiloxane ($S_H$) has a (ε) degree of substitution of all of the amino groups in the range from 40 to 100%, preferably in the range from 50 to 100% and particularly preferably in the range from 60 to 100%, or all of the amino groups of the substituted aminopolyorganosiloxane ($S_H$) are substituted by radicals of the formula (ε) in an amount of from 40 to 100%, preferably 50 to 100% and particularly preferably 60 to 100%.

The reactive hydrogen atoms of the basic amino groups which remain after the reaction of (S) with (H) can optionally be replaced at least partially (e.g. 5 to 100%, in particular 10 to 90%) by means of acylation with acyl radicals of aliphatic monocarboxylic acids, preferably those with 2-4 carbon atoms, or be replaced by means of alkylation and/or benzylation with methyl or ethyl or benzyl. Depending on the amino groups present and the alkylating and/or benzylating agents used, the alkylation and/or benzylation can optionally lead to corresponding secondary or tertiary amino groups or as far as the quaternary ammonium stage. Basic amino groups which are not quaternized may optionally be protonated.

The preferred groups originating from the Si-bonded aminoalkyl groups or amino-mono- or -oligo(alkylenamino)alkyl groups, in particular from the Si-bonded groups (α), reacted with (H) and optionally acylated and/or optionally further alkylated and/or benzylated may be represented by the following average formula $$R_1 \!-\!\!(\!O\!-\!X\!)_{\!q}\!-\!O\!-\!CH_2\!-\!\underset{OH}{CH}\!-\!CH_2\!-\!\underset{(R_3)_m}{N^{m+}}\!-\!\!\left[\!Y_2\!-\!\underset{(R_5)_n}{N^{n+}}\!\right]_{\!p}\!\!-\!Y_1\!-\!,$$

$$(m + p \cdot n) A^-$$

(β)

in which
m is 0 or 1,
n is 0 or 1,
$R_2$ is hydrogen, $C_{1\text{-}2}$-alkyl, benzyl, or a radical of the formula (ε') or,
if m=0, also a radical of the formula $R_6$—CO—,
$R_3$ is hydrogen or, if $R_2$ is $C_{1\text{-}2}$-alkyl, benzyl or a radical of the formula (ε'), also $C_{1\text{-}2}$-alkyl or benzyl,
$R_4$ is hydrogen, $C_{1\text{-}2}$-alkyl, benzyl, a radical of the formula (ε') or,
if n=0, also a radical of the formula $R_6$—CO—,
$R_5$ is hydrogen or, if $R_4$ is $C_{1\text{-}2}$-alkyl or a radical of the formula (ε'), also $C_{1\text{-}2}$-alkyl or benzyl,
$R_6$ is $C_{1\text{-}3}$-alkyl
and $A^-$ is a monovalent anion,
with the provisos that
at least 50% of the q alkylene groups in the meaning of X are ethylene and the radicals of the formula (β) comprise on average at least 1.5 radicals of the formula (ε') per radical of the formula (β).

Preferred groups originating from the groups of the formula (α') or (α") can be represented by the following average formulae $$R_1\!-\!\!(\!O\!-\!X\!)_{\!q}\!-\!O\!-\!CH_2\!-\!\underset{OH}{CH}\!-\!CH_2\!-\!\underset{(R_3)_m}{N^{m+}}\!-\!\!\left[\!CH_2\!-\!CH_2\!-\!\underset{(R_5)_n}{N^{n+}}\!\right]_{\!p}\!\!-\!CH_2\!-\!CH\!\!\begin{array}{c}CH_2\!-\!\\ (CH_2)_r\!-\!H\end{array}\!\!\text{ and}$$

$$(m + p \cdot n) A^-$$

(β')

$$R_1\!-\!\!(\!O\!-\!X\!)_{\!q}\!-\!O\!-\!CH_2\!-\!\underset{OH}{CH}\!-\!CH_2\!-\!\underset{(R_3)_m}{N^{m+}}\!-\!CH_2\!-\!CH_2\!-\!\underset{(R_5)_n}{N^{n+}}\!-\!CH_2\!-\!CH\!\!\begin{array}{c}CH_2\!-\!\\ (CH_2)_r\!-\!H\end{array}$$

$$(m + n) A^-$$

(β")

where preferably at least one $R_2$ and $R_4$ is also a radical of the formula (ε').

Of these, preference is also given to the nonquaternized derivatives, particularly those of the formula

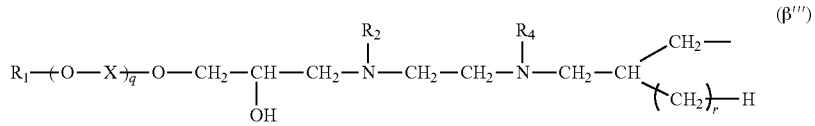

and protonated derivatives thereof.

The substituted derivatives prepared from the Si-bonded aminoalkyl groups or amino-mono- or -oligo(alkylenamino) alkyl groups in particular of the formula (α) by the above-described reaction, in particular of the formula (β), comprise the respective substituents in a distribution corresponding to the preparation. For example, the preferred groups (β″) originating from the radicals of the formula (α″) can principally be represented by the following formulae:

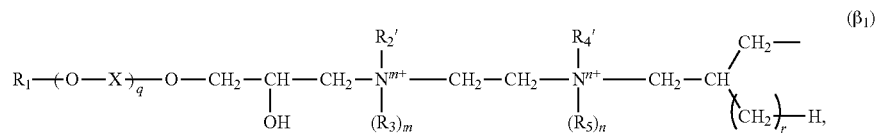

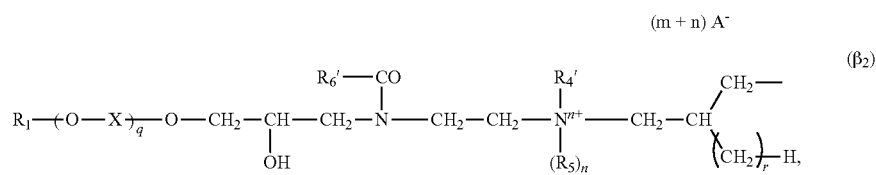

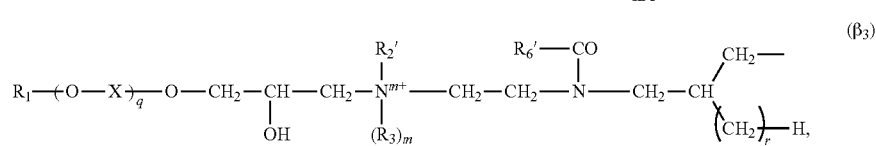

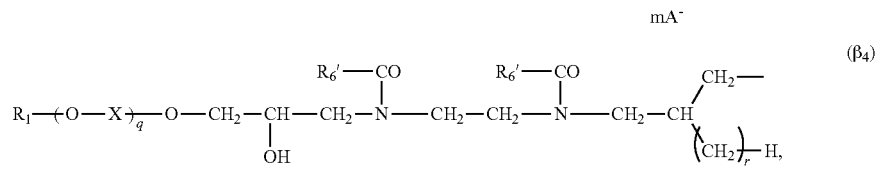

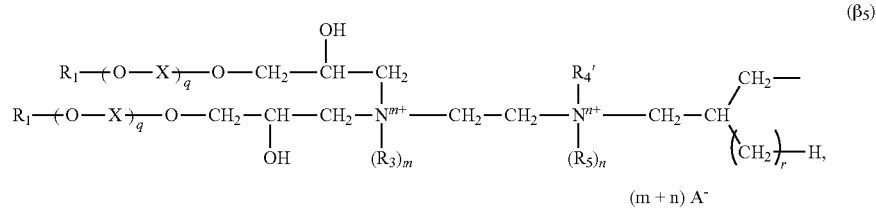

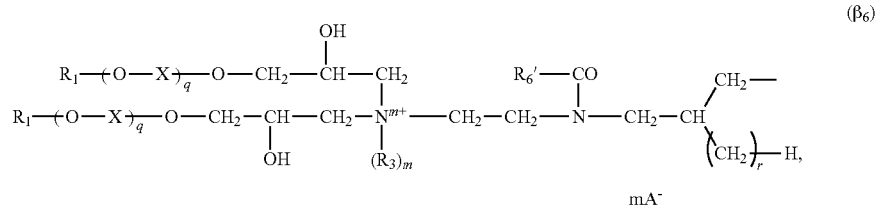

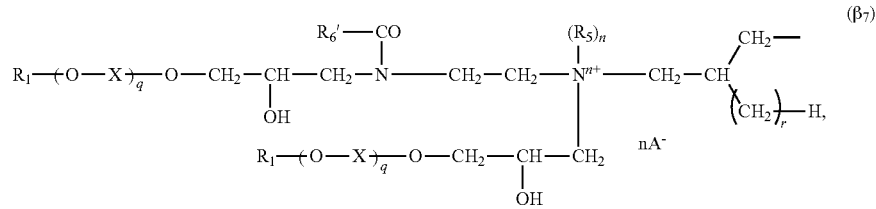

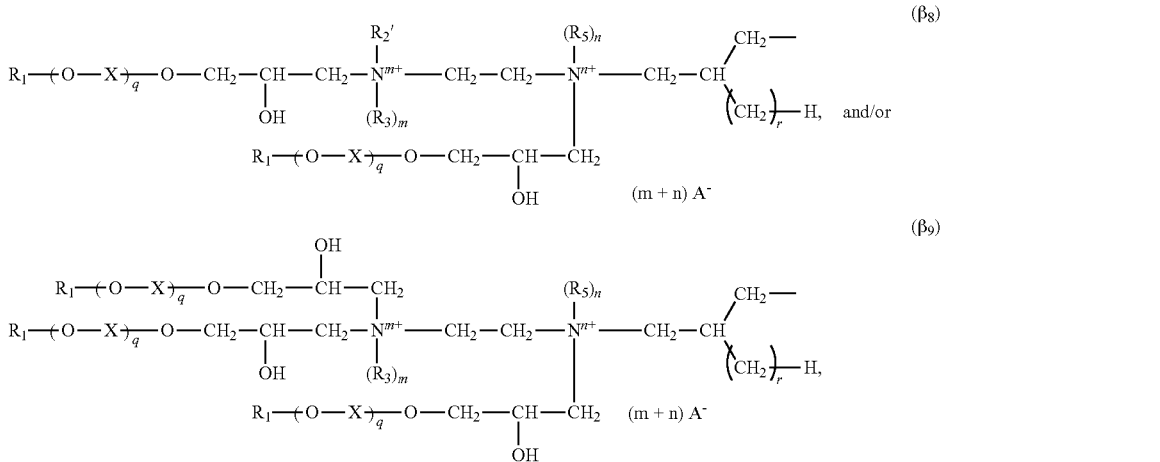

in which $R_{2'}$ is hydrogen, methyl, ethyl or benzyl, $R_{4'}$ is hydrogen, methyl, ethyl or benzyl and $R_6$ is methyl or ethyl.

In the aminopolysiloxanes (S) reacted to exhaustion or virtually to exhaustion with (H), those which predominate accordingly comprise (p+2) radicals of the formula ($\epsilon$), preferably ($\epsilon'$), among those of the above formulae ($\beta_1$) to ($\beta_9$) plus those of the formula ($\beta_9$), and can be accompanied by correspondingly smaller amounts of ones substituted to a lesser degree by ($\epsilon$) or ($\epsilon'$), particularly those of the formulae ($\beta_5$) and/or ($\beta_8$).

In those reacted to a lower degree of conversion with (H), e.g. in those in which 50 to 75% of the replaceable nitrogen-bonded hydrogen atoms of ($\alpha$), particularly in which p is 1 or 2, preferably of ($\alpha'$) or ($\alpha''$), are replaced by radicals of the formula ($\epsilon$) or ($\epsilon'$), and the ones remaining are optionally acylated and/or alkylated and/or benzylated, those which predominate accordingly comprise 2 to (p+1) radicals of the formula ($\epsilon$), preferably ($\epsilon'$), among those of the above formulae ($\beta_1$) to ($\beta_9$) thus those of the formulae ($\beta_5$), ($\beta_6$), ($\beta_7$) and/or ($\beta_8$), besides smaller fractions of ($\beta_9$) and/or ($\beta_1$), ($\beta_2$), ($\beta_3$) and/or ($\beta_4$).

Those originating from Si-bonded aminoalkyl radicals, particularly from the radicals of the formula

 ($\alpha'''$)

in particular

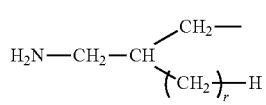 ($\alpha''''$)

are advantageously reacted to exhaustion or almost to exhaustion with (H) so that those disubstituted with radicals ($\epsilon$) or ($\epsilon'$) predominate, or in the preferred ones originating from ($\alpha''''$), primarily the radicals of the formula

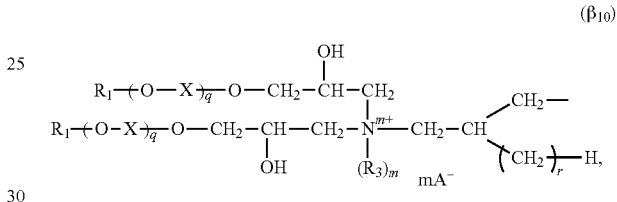

predominate, and in the product comparatively smaller fractions of ones monosubstituted by radicals of the formula ($\epsilon$) or ($\epsilon'$) may optionally be present, in particular in the preferred ones originating from ($\alpha''''$), mainly the radicals of the formula

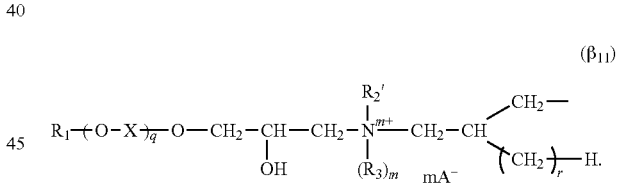

Suitable starting polysiloxanes (S) are any amino-substituted polysiloxanes which comprise corresponding Si-bonded aminoalkyl groups or amino-mono- or -oligo(alkylenamino)alkyl groups. In general, any corresponding aminopolysiloxanes with polycationic or polybasic character are generally suitable, essentially those which are constructed from repeat dimethylsiloxy units and aminosiloxy units. They can have a linear structure or else a branched and/or crosslinked structure (e.g. branched or crosslinked one or more times). The end groups can comprise a reactive substituent, in particular e.g. hydroxy or alkoxy, or may also be blocked; e.g. with trimethylsiloxy. According to a further variant, the end groups can also comprise the abovementioned aminoalkyl groups or amino-mono- or -oligo(alkylenamino)alkyl groups.

Preferably, the aminopolysiloxanes (S) are constructed from repeat units of the following formulae:

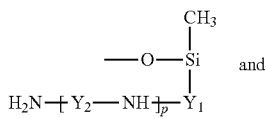 (γ₁)

-continued

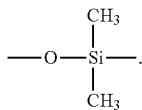 (γ₂)

The end groups preferably correspond to the formulae:

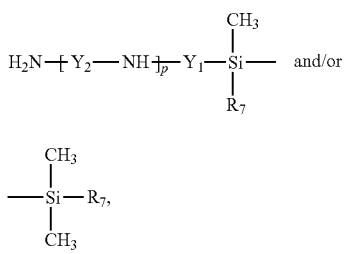 (γ₃) and/or (γ₄)

in which $R_7$ is methyl, hydroxyl, methoxy or ethoxy.

If appropriate, (S) can also comprise Si-branched units of the formula

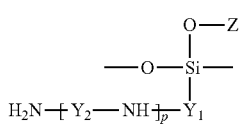 (γ₅)

in which Z is an Si-bonded (poly)siloxane or silyl radical which comprises one or more groups of the formula (γ₁), (γ₂), (γ₃) and/or (γ₄) and optionally further such Si branches and/or crosslinks (e.g. branched and/or crosslinked one or more times).

The aminopolyorganosiloxanes (S) can be characterized by per se customary typical characteristic values, e.g. by their average molecular weight and the content of amine nitrogen, and also by their viscosity. The average molecular weight and the content of amine nitrogen in the aminopolyorganosiloxanes (S) can vary within wide ranges with those having a low amine number being primarily suitable for the purposes of the invention, particularly those with an amine number ≤3.

The aminopolysiloxanes (S) advantageously have a viscosity in the range 500-30 000, primarily 200-20 000, preferably 300-3000 cP (Brookfield rotary viscometer RV, spindle No. 5, 20° C.). The amine number of (S) is advantageously in the range from 0.05 to 3, preferably 0.1 to 2, particularly preferably 0.15 to 1.

Schematically, the aminopolysiloxanes (S) consisting of the abovementioned units can be represented in particular by the following average generic formula:

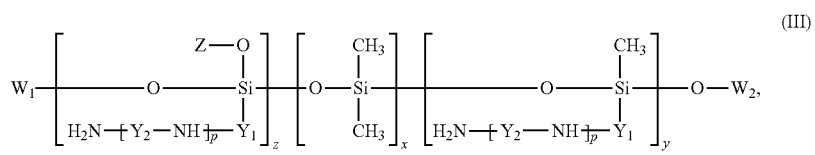 (III)

in which $W_1$ and $W_2$ are in each case a group of the formula (γ₃) or (γ₄), the molecule has at least one group of the formula (α) or (γ₁), (γ₃) and/or (γ₅) and the indices x, y and z are chosen such that the polymer has the values given above for amine number, viscosity and molecular weight. [The above formula (III) serves to illustrate the monomer units present and their number, but not their distribution or position within the polymer molecule]. The ratio of the number of dimethylsiloxy units to the number of aminoalkylsiloxy units and/or amino-mono- or -oligo(alkylenamino)alkylsiloxy units, in particular of the formula

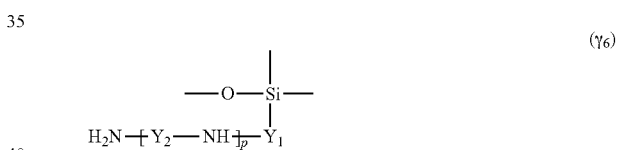 (γ₆)

is advantageously in the range from 3/1 to 600/1, preferably 10/1 to 200/1.

For the copolymerization, the silanes containing amino groups are preferably copolymerized with α,ω-dihydroxypolydimethylsiloxane, advantageously having an average molecular weight $\overline{M}_w$ in the range from 500 to 10 000, preferably 1000 to 7000, or with cyclic siloxanes, e.g. hexamethylcyclotrisiloxane, octamethylcyclotetrasiloxane, decamethylcyclopentasiloxane, dodecamethylcyclohexasiloxane and technical-grade mixtures of two or more thereof. Suitable silanes are primarily trimethoxy- or -ethoxysilanes or dimethoxy- or -ethoxymethylsilanes aminoalkyl-substituted or amino-mono- or -oligo(alkylenamino)alkyl-substituted at Si, in which the Si-bonded aminoalkyl group or amino-mono- or -oligo(alkylenamino)alkyl group corresponds primarily to the formula (α), preferably (α'), particularly (α").

If an amino group-containing trimethoxysilane is used for introducing the units of the formula (γ₁), then, depending on the reaction conditions, the methoxy group can be hydrolyzed to the hydroxyl group or at this point branching of the copolymer can take place, as shown by formula (γ₅).

Depending on the preparation conditions chosen, the amino group-containing units in the molecule—e.g. in the molecule of the formula (III)—can be randomly distributed or be terminal or be grouped as in block polymers or else collect toward the extremities of the linear chains.

For the preparation of the polysiloxanes ($S_H$) used according to the invention in cosmetic and pharmaceutical compositions, preference is given to those polysiloxanes (S) which have an optionally branched, predominantly linear structure of the polysiloxane basic law in which the units of the formula ($\gamma_2$) predominate besides units of the formula ($\gamma_1$).

Preference is given to polysiloxanes in which the Si-bonded aminoalkyl groups or amino-mono- or -oligo(alkylenamino)alkyl groups present, in particular the groups of the formula ($\alpha$) or ($\alpha'$) or ($\alpha''$), are correspondingly substituted on the nitrogen by introducing the radicals ($\epsilon$) or ($\epsilon'$) and optionally further substituents, as described in WO 02/092666. The polysiloxanes comprise in particular repeat units of the formulae

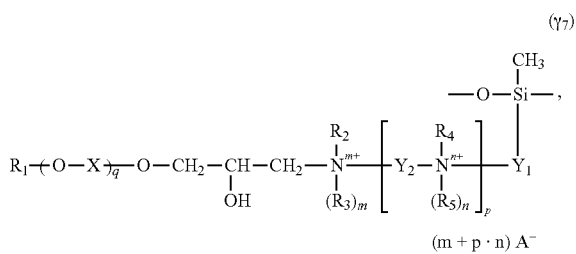

and ($\gamma_2$), and terminal oxygen-bonded silyl groups of the formula ($\gamma_3$) and/or

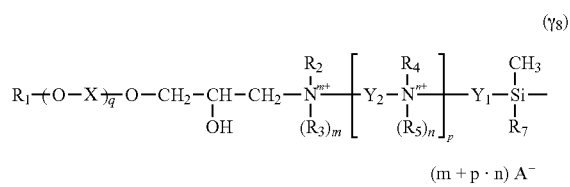

and, if the starting polysiloxanes (S) comprise branches, in particular as in the formula ($\gamma_5$), also correspondingly branched groups, in particular those of the formula

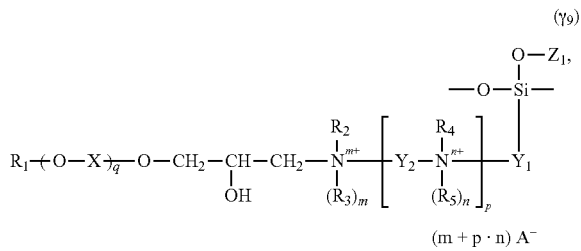

in which $Z_1$ is an Si-bonded (poly)siloxane or silyl radical which comprises one or more of the groups of the formula ($\gamma_2$), ($\gamma_4$), ($\gamma_7$) and/or ($\gamma_8$) and optionally further such Si branches,
with the condition that in the molecule on average at least 1.5, advantageously at least 1.8, preferably at least two, radicals of the formula ($\epsilon$) per overall present Si-bonded aminoalkyl- or amino-mono- or -oligo(alkylenamino)alkyl group of the formulae (3) are present. If, in the above-described polysiloxanes in the radicals of the formula ($\beta$), m and/or n are at least partly equal to 0 and the corresponding substituent $R_2$ or $R_4$ is not an acyl radical $R_6$—CO—, these radicals and the polysiloxanes can, if desired, be protonated.

The average molecular weight of the substituted aminopolyorganosiloxanes ($S_H$) used according to the invention in cosmetic and pharmaceutical compositions can vary within a wide range, e.g. depending on the starting materials, quantitative ratios of the reagents and the reaction conditions chosen, in particular polymerization and substitution conditions, e.g. in the range from 15 000 to 2 000 000, advantageously from 30 000 to 1 750 000, preferably from 50 000 to 1 500 000. The nitrogen content of ($S_H$)—in particular amino groups originating from the amino groups in (S) by reaction with (H) and optionally further substitution to substituted amino and/or ammonium groups and optionally amide groups and also including, if appropriate, remaining unreacted amino groups—is preferably low and is advantageously in the range from 0.03 to 4.2% by weight, advantageously in the range from 0.1 to 2.8% by weight and preferably in the range from 0.16 to 1.4% by weight.

The aminopolyorganosiloxanes ($S_H$) used according to the invention in cosmetic or pharmaceutical compositions have marked hydrophilicity which can be modified through the incorporation of corresponding groups and substituents. Moreover, the above-described aminopolyorganosiloxanes ($S_H$) have a self-emulsifying effect and are compatible with lipophilic components and oils.

Preferred embodiments of the compositions according to the invention are fluids, gels, oils, foams, sprays, lotions, cream gels, creams and powders.

The emulsions may either be water-in-oil emulsions or oil-in-water emulsions, microemulsions, nanoemulsions and multiple emulsions. The emulsions can be prepared in a known manner, i.e. for example by cold, hot, hot/cold or PIT emulsification.

Good substantivity, conditioning effect, and shine-imparting and volumizing effects of the above-described aminopolyorganosiloxanes ($S_H$) are utilized according to the invention for producing hair-treatment compositions, preferably shampoos, hair conditioners, hair treatments, styling compositions, hair rinses, volume spray, styling fluid, hair foam, hair gel, setting composition, hairspray, mousse, hair oils and end fluids.

Aminopolyorganosiloxanes ($S_H$) improve the color absorption behavior of hair colorants and are thus valuable constituents in hair tints and colorants. At the same time, being color protection additives, they additionally improve the durability of hair tints or permanent hair colorants.

The invention thus also provides the use of a cosmetic or pharmaceutical composition according to the invention for the protection and retention of the color in colored keratin fibers, preferably in colored human hair. Preferably, the composition according to the invention comprises for this use from 0.01 to 10% by weight, based on the finished composition, of substituted aminopolyorganosiloxane ($S_H$).

Conditioning effects and good skin sensory properties of skincare compositions and skin-cleansing compositions are achieved by the above-described aminopolyorganosiloxanes ($S_H$).

In a further preferred embodiment of the invention, the cosmetic or pharmaceutical compositions are rinse-off products, in particular shower baths, shower gels or foam baths.

In a further preferred embodiment of the invention, the cosmetic or pharmaceutical compositions are leave-on products, in particular day creams, night creams, care creams, nutrient creams, body lotions, ointments or lipcare compositions.

Further preferred leave-on products are decorative cosmetics, in particular make-ups, eyeshadows, lipsticks or mascara.

In a further preferred embodiment of the invention, the cosmetic and pharmaceutical compositions are sunscreen compositions. These comprise one or more UV filters.

In a further preferred embodiment of the invention, the cosmetic and pharmaceutical compositions are deodorants and antiperspirants, in particular in the form of sprays, sticks, gels or lotions.

In a further preferred embodiment of the invention, the cosmetic and pharmaceutical compositions are surfactant-free compositions, in particular surfactant-free solid compositions or surfactant-free emulsions.

In a further preferred embodiment of the invention, the cosmetic or pharmaceutical compositions are additives for permanent waving compositions, in particular conditioners.

The aqueous-based or aqueous-alcoholic-based cosmetic or pharmaceutical compositions according to the invention comprise aminopolyorganosiloxanes ($S_H$) preferably in the amounts by weight of from 0.01 to 30%, particularly preferably from 0.2 to 10%, especially preferably from 0.5 to 2%, based on the finished compositions.

The cosmetic or pharmaceutical compositions according to the invention in anhydrous form based on oils comprise aminopolyorganosiloxanes ($S_H$) preferably in the amounts by weight of from 0.01 to 80%, particularly preferably from 0.05 to 60%, especially preferably from 0.1 to 50%, based on the finished compositions.

The cosmetic or pharmaceutical compositions according to the invention in the form of an emulsion comprise substituted aminopolyorganosiloxanes ($S_H$) preferably in amounts by weight of from 0.01 to 30%, particularly preferably from 0.05 to 10% and especially preferably from 0.1 to 5%, based on the finished composition.

In a further preferred embodiment, the compositions according to the invention are oil-in-water emulsions with a water fraction of from 5 to 95% by weight, preferably 15 to 75% by weight, particularly preferably 25 to 85% by weight.

In a further preferred embodiment, the compositions according to the invention are water-in-oil emulsions with an oil fraction of from 5 to 95% by weight, preferably 15 to 75% by weight, particularly preferably 25 to 65% by weight.

For the compositions according to the invention on an aqueous-alcoholic or alcoholic basis, all mono- or polyhydric alcohols are suitable. Preference is given to alcohols having 1 to 4 carbon atoms, such as ethanol, propanol, isopropanol, n-butanol, isobutanol, t-butanol or glycerol, and alkylene glycols, in particular propylene glycol, butylene glycol or hexylene glycol, and mixtures of said alcohols. Further preferred alcohols are polyethylene glycols with a relative molecular mass below 2000. In particular, a use of polyethylene glycol with a relative molecular mass between 200 and 600 and of polyethylene glycol with a relative molecular mass between 400 and 600 is preferred.

The oil-based compositions according to the invention can preferably comprise: hydrocarbon oils with linear or branched, saturated or unsaturated $C_7$-$C_{40}$-carbon chains, for example dodecane, isododecane, cholesterol, hydrogenated polyisobutylenes, docosanes, hexadecane, isohexadecane, paraffins and isoparaffins, but also triglycerides of animal and vegetable origin, for example beef tallow, pig fat, goose grease, perhydrosqualene, lanolin, sunflower oil, maize oil, soya oil, rice oil, jojoba oil, babusscu oil, pumpkin oil, grapeseed oil, sesame oil, walnut oil, apricot oil, macadamia oil, avocado oil, sweet almond oil, lady's smock oil, castor oil, olive oil, peanut oil, rapeseed oil and coconut oil and synthetic oils, such as purcellin oil, linear and/or branched fatty alcohols and fatty acid esters, preferably Guerbet alcohols having 6 to 18, preferably 8 to 10, carbon atoms; esters of linear ($C_6$-$C_{13}$)-fatty acids with linear ($C_6$-$C_{20}$)-fatty alcohols; esters of branched ($C_6$-$C_{13}$)-carboxylic acids with linear ($C_6$-$C_{20}$)-fatty alcohols, esters of linear ($C_6$-$C_{18}$)-fatty acids with branched alcohols, in particular 2-ethylhexanol; esters of linear and/or branched fatty acids with polyhydric alcohols (such as e.g. dimerdiol or trimerdiol) and/or Guerbet alcohols; alcohol esters of $C_1$-$C_{10}$-carboxylic acids or $C_2$-$C_{30}$-dicarboxylic acids, esters, such as dioctyl adipate, diisopropyl dimer dilineolate; propylene glycols/dicaprylate or waxes, such as beeswax, paraffin wax or microcrystalline waxes, optionally in combination with hydrophilic waxes, such as, for example, cetylstearyl alcohol; fluorinated and perfluorinated oils; monoglycerides of $C_1$-$C_{30}$-carboxylic acids, diglycerides of $C_1$-$C_{30}$-carboxylic acids, triglycerides of $C_1$-$C_{30}$-carboxylic acids, for example triglycerides of caprylic/capric acids, ethylene glycol monoesters of $C_1$-$C_{30}$-carboxylic acids, ethylene glycol diesters of $C_1$-$C_{30}$-carboxylic acids, propylene glycol monoesters of $C_1$-$C_{30}$-carboxylic acids, propylene glycol diesters of $C_1$-$C_{30}$-carboxylic acids, and propoxylated and ethoxylated derivatives of the abovementioned classes of compound. The carboxylic acids can comprise linear or branched alkyl groups or aromatic groups. By way of example, mention may be made of diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenate, dioctyl maleate, dioctyl sebacate, cetyl octanoate, diisopropyl dilinoleate, caprylic/capryl triglyceride, PEG-6 caprylic/capryl triglyceride, PEG-8 caprylic/capryl triglyceride, cetyl ricinoleate, cholesterol hydroxystearate, cholesterol isostearate, $C_1$-$C_{30}$-monoesters and polyesters of glycerol, for example glyceryl tribehenate, glyceryl stearate, glyceryl palmitate, glyceryl distearate, glyceryl dipalmitate, $C_1$-$C_{30}$-carboxylic monoesters and polyesters of sugars, for example glucose tetraoleate, glucose tetraesters of soya oil fatty acid, mannose tetraesters of soya oil fatty acid, galactose tetraesters of oleic acid, arabinose tetraesters of linoleic acid, xylose tetralinoleate, galactose pentaoleate, sorbitol tetraoleate, sorbitol hexaesters of unsaturated soya oil fatty acid, xylitol pentaoleate, sucrose tetraoleate, sucrose pentaoleate, sucrose hexaoleate, sucrose heptaoleate, sucrose oleate.

The silicone oils available are preferably dimethylpolysiloxanes and cyclomethicones, polydialkylsiloxanes $R_3SiO(R_2SiO)_xSiR_3$, where R is methyl or ethyl, particularly preferably methyl, and x is a number from 2 to 500, for example the dimethicones available under the trade names VICASIL (General Electric Company), DOW CORNING 200, DOW CORNING 225, DOW CORNING 200 (Dow Corning Corporation), trimethylsiloxysilicates $[(CH_3)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example the polymethylphenylsiloxanes available under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty acid-, alcohol-, polyether-, epoxy-, fluorine- and/or alkyl-modified silicone compounds, and polyether siloxane copolymers.

The hair colorants and tints according to the invention preferably comprise direct dyes and/or oxidation dye precursors in the customary pH ranges. Suitable direct dyes are preferably nitroaniline derivatives, such as 1-[(2-hydroxyethyl)amino]-2-nitrobenzene (Velsol® Yellow 2), 4-hydroxypropylamino-3-nitrophenol (Velsol® Red BN), 3-nitro-p-hydroxyethylaminophenol (Velsol® Red 54), 4-hydroxyethylamino-3-nitroaniline (Velsol® Red 3), N,N'-bis(hydroxyethyl)-2-nitro-p-phenylenediamine (Velsol® Violet BS), N,N',N'-tris(hydroxyethyl)-2-nitro-p-phenylenediamine (Velsol® Blue 2), 4-(2'-hydroxyethyl)amino-3-nitrotoluene, 4-(2'-hydroxyethyl)amino-3-nitrobenzyl alcohol, 4-(2'-hydroxyethyl)amino-3-nitro-1-trifluoromethylbenzene, 4-(2',3'-dihydroxy-propyl)amino-3-nitrochlorobenzene, 4-(2'-hydroxyethyl)amino-3-nitrobromobenzene and 4-(2',3'-dihydroxypropyl)amino-3-nitrobromobenzene, nitrobenzene derivatives, for example 2-amino-4-nitrophenol, picramic acid, 1-[(2'-hydroxyethyl)amino]-2-amino-4-nitrobenzene, 2-nitro-4-[(2'-hydroxyethyl)amino]aniline, 4-bis[(2'-hydroxyethyl)amino]-1-methylamino-2-nitrobenzene, 2,5-bis[(2'-hydroxyethyl)amino]nitrobenzene, 2-(2'-hydroxyethyl)amino-4,6-dinitrophenol, 1-amino-4-(2',3'-dihydroxypropyl)amino-2-nitro-5-chlorobenzene, but also triphenylmethane dyes such as, for example, Basic Violet 1 (C.I. 42535), azodyes, such as, for example, Acid Brown 4 (C.I. 14805), anthraquinone dyes such as, for example, Disperse Blue 23 (C.I. 61545), Disperse Violet 4 (C.I. 61105), 1,4,5,8-tetraminoanthraquinone and 1,4-diaminoanthraquinone and further direct dyes.

Oxidation dye precursors which are available are preferably p-phenylenediamines and p-aminophenols and derivatives thereof, such as, for example, p-tolylenediamine, p-phenylenediamine, p-aminophenol, which are combined with so-called modifiers or couplers, such as, for example, m-phenylenediamine, resorcinol, m-aminophenol and derivatives thereof for the purpose of nuancing the coloration.

Suitable oxidizing agents for developing the hair colorations are preferably hydrogen peroxide and its addition compounds.

To increase the color intensity, the compositions according to the invention can comprise the carriers customary in cosmetic systems, in particular benzyl alcohol, vanillin (4-hydroxy-3-methoxybenzaldehyde), isovanillin, p-hydroxyanisol, 3-hydroxy-4-methoxybenzaldehyde, 2-phenoxyethanol, salicylaldehyde, 3,5-dihydroxybenzaldehyde, 3,4-dihydroxybenzaldehyde, 4-hydroxyphenylacetamide, methyl p-hydroxy-benzoate, p-hydroxybenzaldehyde, m-cresol, hydroquinone monomethyl ether, o-fluorophenol, m-fluorophenol, p-fluorophenol, 2-(2'-hydroxyphenoxy)ethanol, 3,4-methylenedioxyphenol, resorcinol monomethyl ether, 3,4-dimethoxyphenol, 3-trifluoromethylphenol, resorcinol monoacetate, ethylvanillin, 2-thiophenethanol, butyl lactate and butyl glycolate. Of particular advantage with a synergistic effect are compositions according to the invention comprising phenoxyethanol and/or benzyl alcohol.

The hair colorants according to the invention can advantageously comprise pearlescence-imparting compounds, for example fatty acid monoalkanolamides, fatty acid dialkanolamides, monoesters or diesters of alkylene glycol, in particular ethylene glycol and/or propylene glycol or oligomers thereof with higher fatty acids, e.g. palmitic acid, stearic acid or behenic acid, or mixtures thereof, monoesters or diesters of alkylene glycols with fatty acids, fatty acids and metal salts thereof, monoesters or polyesters of glycerol with carboxylic acids and ketosulfones of various types, preferably ethylene glycol distearate and polyethylene glycol distearate with about 3 glycol units.

The hair-treatment compositions according to the invention preferably comprise 0.1 to 15% by weight, particularly preferably 1 to 10% by weight, of pearlescence-imparting compounds.

Glitter and shine effects of the compositions according to the invention can be produced preferably by adding mica, colored polyacrylic esters and mica, mica-iron oxide, mica-titanium oxide and through pigments. Suitable pigments are metal oxides, for example iron oxides, titanium oxide, ultramarine blue, and pigments modified with cationic coating shells, as described in WO 00/12053 and EP 504 066.

As further auxiliaries and additives, the cosmetic compositions according to the invention can comprise surfactants, emulsifiers, cationic polymers, thickeners, film formers, antimicrobial active ingredients, astringents, antioxidants, UV light protection filters, pigments/micropigments, gelling agents, and further additives customary in cosmetics, such as, for example, superfatting agents, moisturizing agents, silicones, stabilizers, conditioning agents, glyceryl, preservatives, pearlizing agents, dyes, fragrance and perfume oils, solvents, hydrotropes, opacifiers, fatty alcohols, substances with a keratolytic and keratoplastic effect, antidandruff agents, biogenic active ingredients (local anesthetics, antibiotics, antiphlogistics, antiallergics, corticosteroids, sebostatics), vitamins, Bisabolol®, Allantoin®, Phytantriol®, Panthenol®, AHA acids, plant extracts, for example aloe vera and proteins.

Anionic washing-active substances which may be mentioned are preferably: $C_{10}$-$C_{20}$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfates, alkanesulfonates, and hydroxyalkanesulfonates, olefinsulfonates, acylesters of isothionates, α-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulforicinoleates, amphoacetates or amphoglycinates, acylglutamates. These compounds and their mixtures are used in the form of their water-soluble or water-dispersible salts, for example the sodium, potassium, magnesium, ammonium, mono-, di- and triethanolammonium and analogous alkylammonium salts.

The weight fraction of the anionic surfactants is preferably 1 to 30% by weight, particularly preferably 5 to 25% by weight, especially preferably 10 to 22% by weight, based on the finished compositions.

Suitable cationic surfactants are, for example, quaternary ammonium salts, such as di($C_{10}$-$C_{24}$-alkyl)dimethylammonium chloride or bromide, preferably di($C_{12}$-$C_{18}$-alkyl)dimethylammonium chloride or bromide; $C_{10}$-$C_{24}$-alkyldimethylethylammonium chloride or bromide $C_{10}$-$C_{24}$ alkyltrimethylammonium chloride or bromide, preferably cetyltrimethylammonium chloride or bromide and $C_{20}$-$C_{22}$-alkyltrimethylammonium chloride or bromide; $C_{10}$-$C_{24}$-alkyldimethylbenzylammonium chloride or bromide, preferably $C_{12}$-$C_{18}$-alkyldimethylbenzylammonium chloride; N—($C_{10}$-$C_{18}$-alkyl)pyridinium chloride or bromide, preferably N—($C_{12}$-$C_{16}$-alkyl)pyridinium chloride or bromide; N—($C_{10}$-$C_{18}$-alkyl)isoquinolinium chloride, bromide or monoalkylsulfate; N—($C_{12}$-$C_{18}$-alkyl)polyoylaminoformylmethyl)pyridinium chloride; N—($C_{12}$-$C_{18}$-alkyl)-N-methyl-morpholinium chloride, bromide or monoalkylsulfate; N—($C_{12}$-$C_{18}$-alkyl)-N-ethylmorpholinium chloride, bromide or monoalkylsulfate; $C_{16}$-$C_{18}$-alkylpentaoxyethylammonium chloride; diisobutylphenoxyethoxyethyldi-methylbenzylammonium chloride; salts of N,N-diethylaminoethylstearylamide and -oleylamide with hydrochloric acid, acetic acid, lactic acid, citric acid, phosphoric acid; N-acylaminoethyl, N,N-diethyl-N-methylammonium chloride, bromide or monoalkylsulfate and N-acylaminoethyl-N,N-diethyl-N-benzylammonium chloride, bromide or monoalkylsulfate, where acyl is preferably stearyl or oleyl.

The weight fraction of the cationic surfactants is preferably 0.1 to 10% by weight, particularly preferably 0.2 to 7% by weight, especially particularly preferably 0.5 to 5% by weight, based on the finished composition.

Suitable nonionic surfactants which can be used as washing-active substances are preferably fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acyl polyethylene glycols); polypropylene glycol ethoxylates (Pluronics®); fatty acid amide polyethylene glycols; N-alkyl-, N-alkoxypolyhydroxy fatty acid amide, in particular fatty acid N-methyl-glucamides, sucrose esters; polyglycol ethers, alkyl polyglycosides, phosphoric esters (mono-, di- and triphosphoric esters ethoxylated and nonethoxylated).

The weight fraction of the nonionic surfactants in the compositions according to the invention (e.g. in the case of rinse-off products) is preferably in the range from 1 to 20% by weight, particularly preferably 2 to 10% by weight, especially preferably 3 to 7% by weight, based on the finished composition.

Preferred amphoteric surfactants are: N—($C_{12}$-$C_{18}$-alkyl)-β-aminopropionates and N—($C_{12}$-$C_{18}$-alkyl)-β-iminodipropionates as alkali metal and mono-, di- and trialkylammonium salts; N-acylaminoalkyl-N,N-dimethylacetobetaine, preferably N—($C_8$-$C_{18}$-acyl)aminopropyl-N,N-dimethylacetobetaine; $C_{12}$-$C_{18}$-alkyldimethylsulfopropylbetaine, amphoteric surfactants based on imidazoline (trade name: Miranol®, Steinapon®), preferably the sodium salt of 1-(β-carboxymethyloxyethyl)-1-(carboxymethyl)-2-laurylimidazolinium; amine oxides, e.g. $C_{12}$-$C_{18}$-alkyldimethylamine oxide, fatty acid amidoalkyldimethylamine oxide.

The weight fraction of the amphoteric surfactants is preferably 0.5 to 20% by weight, particularly preferably 1 to 10% by weight, based on the finished composition.

Furthermore, foam-boosting cosurfactants from the group consisting of alkylbetaines, alkylamidobetaines, aminopropionates, aminoglycinates, imidazoliniumbetaines and sulfobetaines, amine oxides and fatty acid alkanolamides or polyhydroxyamides can be used in the compositions according to the invention.

Preferred surfactants in the compositions according to the invention are alkyl ether sulfates, alkylsulfates, in particular laurylsulfate, alkylbetaines, in particular cocoamidopropylbetaine, amphoacetates, acylglutamates, in particular sodium cocoylglutamate, alkyl ether sulfosuccinates, in particular disodium laureth sulfosuccinate and coconut fatty acid diethanolamide.

The total amount of the surfactants used in the compositions according to the invention is preferably 1 to 70% by weight, particularly preferably 10 to 40% by weight, especially preferably 12 to 35% by weight, based on the finished composition.

Compositions according to the invention in the form of emulsions can be produced without further emulsifier or else comprise one or more emulsifiers. These emulsifiers can be chosen from the group of nonionic, anionic, cationic or amphoteric emulsifiers.

Suitable nonionogenic coemulsifiers are preferably addition products of from 0 to 30 mol of ethylene oxide and/or 0 to 5 mol of propylene oxide onto linear fatty alcohols having 8 to 22 carbon atoms, onto fatty acids having 12 to 22 carbon atoms, only alkylphenols having 8 to 15 carbon atoms in the alkyl group and onto sorbitan or sorbitol esters; ($C_{12}$-$C_{18}$) fatty acid monoesters and diesters of addition products of from 0 to 30 mol of ethylene oxide onto glycerol; glycerol monoesters and diesters and sorbitan monoesters and diesters of saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol and, in particular, polyglycerol, esters, such as, for example, polyglycerol polyricinoleate and polyglycerol poly-12-hydroxystearate. Likewise preferably suitable are ethoxylated fatty amines, fatty acid amides, fatty acid alkanolamides and mixtures of compounds of two or more of these classes of substance.

Suitable ionogenic coemulsifiers are, for example, anionic emulsifiers, such as mono-, di- or triphosphoric esters, soaps (e.g. sodium stearate), fatty alcohol sulfates, but also cationic emulsifiers, such as mono-, di- and trialkylquats and polymeric derivatives thereof.

Available amphoteric emulsifiers are preferably alkylaminoalkylcarboxylic acids, betaines, sulfobetaines and imidazoline derivatives.

It is also possible to use naturally occurring emulsifiers, of these preference being given to beeswax, wool wax, lecithin and sterols.

Fatty alcohol ethoxylates are preferably chosen from the group of ethoxylated stearyl alcohols, cetyl alcohols, cetylstearyl alcohols, in particular polyethylene glycol(13) stearyl ether, polyethylene glycol(14) stearyl ether, polyethylene glycol(15) stearyl ether, polyethylene glycol(16) stearyl ether, polyethylene glycol(17) stearyl ether, polyethylene glycol(18) stearyl ether, polyethylene glycol(19) stearyl ether, polyethylene glycol(20) stearyl ether, polyethylene glycol(12) isostearyl ether, polyethylene glycol(13) isostearyl ether, polyethylene glycol(14) isostearyl ether, polyethylene glycol(15) isostearyl ether, polyethylene glycol(16) isostearyl ether, polyethylene glycol(17) isostearyl ether, polyethylene glycol(18) isostearyl ether, polyethylene glycol (19) isostearyl ether, polyethylene glycol(20) isostearyl ether, polyethylene glycol(13) cetyl ether, polyethylene glycol(14) cetyl ether, polyethylene glycol(15) cetyl ether, polyethylene glycol(16) cetyl ether, polyethylene glycol(17) cetyl ether, polyethylene glycol(18) cetyl ether, polyethylene glycol(19) cetyl ether, polyethylene glycol(20) cetyl ether, polyethylene glycol(13) isocetyl ether, polyethylene glycol(14) isocetyl ether, polyethylene glycol(15) isocetyl ether, polyethylene glycol(16) isocetyl ether, polyethylene glycol(17) isocetyl ether, polyethylene glycol(18) isocetyl ether, polyethylene glycol(19) isocetyl ether, polyethylene glycol(20) isocetyl ether, polyethylene glycol(12) oleyl ether, polyethylene glycol(13) oleyl ether, polyethylene glycol(14) oleyl ether, polyethylene glycol(15) oleyl ether, polyethylene glycol(12) lauryl ether, polyethylene glycol(12) isolauryl ether, polyethylene glycol(13) cetylstearyl ether, polyethylene glycol(14) cetylstearyl ether, polyethylene glycol(15) cetylstearyl ether, polyethylene glycol(16) cetylstearyl ether, polyethylene glycol(17) cetylstearyl ether, polyethylene glycol(18) cetylstearyl ether, polyethylene glycol(19) cetylstearyl ether, polyethylene glycol(20) cetylstearyl ether, polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol (19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol (15) oleate, polyethylene glycol(16) oleate, polyethylene glycol(17) oleate, polyethylene glycol(18) oleate, polyethylene glycol(19) oleate, polyethylene glycol(20) oleate.

As ethoxylated alkyl ether carboxylic acid or salts thereof it is advantageously possible to use sodium laureth 11-carboxylate.

An advantageous alkyl ether sulfate is sodium laureth-14 sulfate, and an advantageous ethoxylated cholesterol derivative is polyethylene glycol(30) cholesteryl ether. Preference is likewise given to polyethylene glycol(25) soyasterol.

Ethoxylated triglycerides which can be used advantageously are polyethylene glycol(60) evening primrose glycerides.

It is also advantageous to choose the polyethylene glycol glycerol fatty acid esters from the group consisting of polyethylene glycol(20) glyceryl laurate, polyethylene glycol(6) glyceryl caprate, polyethylene glycol(20) glyceryl oleate, polyethylene glycol(20) glyceryl isostearate and polyethylene glycol(18) glyceryl oleate/cocoate.

Among the sorbitan esters, polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate are particularly suitable.

Advantageous W/O emulsifiers which can be used are the following: fatty alcohols having 8 to 30 carbon atoms, monoglycerol esters of saturated and/or unsaturated, branched and/or unbranched alkanecarboxylic acids with a chain length of from 8 to 24, in particular 12 to 18, carbon atoms, diglycerol esters of saturated and/or unsaturated, branched and/or unbranched alkanecarboxylic acids with a chain length of from 8 to 24, in particular 12 to 18, carbon atoms, monoglycerol ethers of saturated and/or unsaturated, branched and/or unbranched alcohols with a chain length of from 8 to 24, in particular 12 to 18, carbon atoms, diglycerol ethers of saturated and/or unsaturated, branched and/or unbranched alcohols with a chain length of from 8 to 24, in particular 12 to 18, carbon atoms, propylene glycol esters of saturated and/or unsaturated, branched and/or unbranched alkanecarboxylic acids of chain length from 8 to 24, in particular 12 to 18, carbon atoms, and sorbitan esters of saturated and/or unsaturated, branched and/or unbranched alkanecarboxylic acids with a chain length of from 8 to 24, in particular 12 to 18, carbon atoms.

Particularly advantageous W/O emulsifiers are glyceryl monostearate, glyceryl monoisostearate, glyceryl monomyristate, glyceryl monooleate, glyceryl monolaurate, glyceryl monocaprylate, glyceryl monocaprate, diglyceryl monostearate, diglyceryl monoisostearate, propylene glycol monostearate, propylene glycol monoisostearate, propylene glycol monocaprylate, propylene glycol monolaurate, sorbitan monolaurate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol or polyethylene glycol(2) stearyl ether.

The weight fraction of the emulsifier or emulsifiers present in the compositions according to the invention, in addition to the aminopolyorganosiloxane ($S_H$) is preferably 0.1 to 20% by weight, particularly preferably 0.5 to 15% by weight, especially preferably 1 to 10% by weight, based on the finished composition.

Suitable cationic polymers are preferably the compounds known under the INCI name "Polyquaternium", in particular Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, Polyquaternium-37& mineral oil & PPG trideceth (®Salcare SC95), PVP dimethylaminoethyl methacrylate copolymer, guar hydroxypropyltriammonium chlorides, and calcium alginate and ammonium alginate.

Furthermore, the following may preferably be used: cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as, for example, amidomethicones; copolymers of adipic acid and dimethylaminohydroxypropyl-diethylenetriamine; polyaminopolyamide and cationic chitin derivatives, such as, for example, chitosan.

The weight fraction of cationic polymers in the compositions according to the invention can preferably be in the range from 0.1 to 10% by weight, particularly preferably in the range from 0.2 to 5% by weight, especially preferably in the range from 0.5 to 2.5% by weight.

The desired viscosity of the compositions can be adjusted by adding thickeners. Of suitability are preferably cellulose ethers and other cellulose derivatives (e.g. carboxymethylcellulose, hydroxyethylcellulose), gelatin, starch and starch derivatives, sodium alginates, fatty acid polyethylene glycol esters, agar agar, traganth or dextrin derivatives, in particular dextrin esters.

The synthetic polymers used are various materials, preferably polyvinyl alcohols, polyacrylamides, polyvinylamides, polysulfonic acids, in particular copolymers based on ammonium salts of acrylamidoalkylsulfonic acids and cyclic N-vinylcarboxamides or cyclic and linear N-vinylcarboxamides and also hydrophobically modified acrylamidoalkylsulfonic acid copolymers, polyacrylic acid, polyacrylic acid derivatives, polyacrylic esters, polyvinylpyrrolidone, polyvinyl methyl ether, polyethylene oxides, copolymers of maleic anhydride and vinyl methyl ether, and various mixtures and copolymers of the abovementioned compounds, including their various salts and esters. These polymers can, if desired, be crosslinked or uncrosslinked.

Thickeners which are particularly suitable especially for oil-based compositions are dextrin esters, for example dextrin palmitate, but also fatty acid soaps, fatty alcohols and silicone waxes, for example alkylmethicones, SilCare® 41M40, SilCare® 41M50, SilCare® 41M65, SilCare® 41M70 or SilCare® 41M80.

Depending on the intended use, preferred film formers are salts of phenylbenzimidazolesulfonic acid, water-soluble polyurethanes, for example $C_{10}$-polycarbamylpolyglyceryl esters, polyvinyl alcohol, polyvinylpyrrolidone copolymers, for example vinylpyrrolidone/vinyl acetate copolymer, water-soluble acrylic acid polymers/copolymers or esters or salts thereof, for example partial ester copolymers of acrylic/methacrylic acid and polyethylene glycol ethers of fatty alcohols, such as acrylate/steareth-20 methacrylate copolymer, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate, available for example under the trade name Aristoflex® A 60 (Clariant), and polymeric amine oxides, for example representatives available under the trade names Diaformer Z-711, 712, 731, 751.

Preferably suitable antimicrobial active ingredients are cetyltrimethylammonium chloride, cetylpyridinium chloride, benzethonium chloride, diisobutylethoxyethyldimethylbenzylammonium chloride, sodium N-laurylsarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysinehexadecylamide, citrate heavy metal salts, salicylates, piroctose, in particular zinc salts, pyrithiones and heavy metal salts thereof, in particular zinc pyrithione, zinc phenol sulfate, farnesol and combinations of these active substances.

The compositions according to the invention comprise the antimicrobial agents preferably in amounts up to 50% by weight, particularly preferably in amounts of from 0.01 to 10% by weight, particularly preferably in amounts of from 0.1 to 10% by weight.

Preferred astringents are oxides, preferably magnesium oxide, aluminum oxide, titanium dioxide, zirconium dioxide and zinc oxide, oxide hydrates, preferably aluminum oxide hydrate (boehmite) and hydroxides, preferably of calcium, magnesium, aluminum, titanium, zirconium or zinc.

The compositions according to the invention comprise the astringent active ingredients preferably in amounts of from 0 to 50% by weight, particularly preferably in amounts of from 0.01 to 10% by weight and especially preferably in amounts of from 0.1 to 10% by weight.

Advantageous compositions according to the invention comprise one or more antioxidants. Favorable, but nevertheless optional, antioxidants which can be used are all antioxidants which are customary or suitable for cosmetic and/or pharmaceutical application.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol/kg), and also (metal) chelating agents (e.g. α-hydroxyfatty acids, palmitic acid, phytic acid, lactoferrine), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (e.g. vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), superoxide dismutase and the derivatives (salts, esters, ethers, sugars, nucleotides, nucleosides, peptides and lipids) of these specified substances which are suitable according to the invention.

For the purposes of the present invention, water-soluble antioxidants can be used particularly advantageously.

The antioxidants can protect the skin and the hair against oxidative stress. Preferred antioxidants here are vitamin E and derivatives thereof, and vitamin A and derivatives thereof.

The amount of antioxidants (one or more compounds) in the compositions according to the invention is preferably 0.001 to 30% by weight, particularly preferably 0.05 to 20% by weight, in particular 1 to 10% by weight, based on the total weight of the compositions.

If vitamin E and/or derivatives thereof are the antioxidant or the antioxidants, it is advantageous to choose their particular concentrations from the range from 0.001 to 10% by weight, based on the total weight of the compositions.

In a particularly preferred embodiment of the invention, the cosmetic or pharmaceutical compositions comprise antioxidants chosen from superoxide dismutase, tocopherol (vitamin E) and ascorbic acid (vitamin C).

Suitable UV filters are preferably 4-aminobenzoic acid; 3-(4'-trimethylammonium)benzylideneboran-2-one methylsulfate; 3,3,5-trimethyl cyclohexylsalicylate; 2-hydroxy-4-methoxybenzophenone; 2-phenylbenzimidazole-5-sulfonic acid and its potassium, sodium and triethanolamine salts; 3,3'-(1,4-phenylenedimethine)bis(7,7-dimethyl-2-oxobicyclo[2.2.1]heptane-1-methanesulfonic acid and its salts; 1-(4-tert-butylphenyl)-3-(4-methoxyphenyl)propane-1,3-dione, 3-(4'-sulfo)-benzylidenebornan-2-one and its salts; 2-ethylhexyl 2-cyano-3,3-diphenylacrylate; polymers of N-[2(and 4)-(2-oxoborn-3-ylidenemethyl)benzyl]acrylamide; 2-ethylhexyl 4-methoxycinnamate; ethoxylated ethyl4-aminobenzoate; isoamyl 4-methoxycinnamate; 2,4,6-tris[p-(2-ethylhexyloxycarbonyl)anilino]-1,3,5-triazine; 2-(2H-benzotriazol-2-yl)-4-methyl-6-(2-methyl-3-(1,3,3,3-tetramethyl-1-(trimethylsilyloxy)-disiloxanyl)propyl) phenol; bis(2-ethylhexyl) 4,4'-[(6-[4-((1,1-dimethylethyl) aminocarbonyl)phenylamino]-1,3,5-triazin-2,4-yl)diimino] bisbenzoate; 3-(4'-methylbenzylidene)-D,L-camphor; 3-benzylidenecamphor; 2-ethylhexyl salicylate; 2-ethylhexyl 4-dimethylaminobenzoate; hydroxy-4-methoxybenzophenone-5-sulfonic acid (sulisobenzonum) and the sodium salt; and/or 4-isopropylbenzyl salicylate.

Pigments/micropigments which may be used are preferably microfine titanium dioxide, mica-titanium dioxide, iron oxides, mica-iron oxide, zinc oxide, silicon oxides, ultramarine blue, chromium oxides.

Suitable gelling agents are all surface-active substances which, dissolved in the liquid phase, form a network structure and thus consolidate the liquid phase. Suitable gelling agents are specified, for example, in WO 98/58625.

Preferred gelling agents are metal salts of fatty acids, preferably with 12 to 22 carbon atoms, for example sodium stearate, sodium palmitate, sodium laurate, sodium arachidate, sodium behenate, potassium stearate, potassium palmitate, sodium myristate, aluminum monostearate, hydroxyfatty acids, for example 12-hydroxystearic acid, 16-hydroxyhexadecanoyl acid; fatty acid amides; fatty acid alkanolamides; dibenzalsorbitol and alcoholic polyamides and polyacrylamides or mixtures thereof.

Preferably, the compositions according to the invention comprise 0.01 to 20% by weight, particularly preferably 0.1 to 10% by weight, especially preferably 1 to 8% by weight and very particularly preferably 3 to 7% by weight, of gelling agents.

Further additives may be silicone compounds, preferably dimethylpolysiloxane, methylphenylpolysiloxanes, cyclic silicones, and amino-, fatty acid-, alcohol-, polyether-, epoxy-, fluorine- and/or alkyl-modified silicone compounds, for example alkylsilicones SilCare® Silicone 41M10, SilCare® Silicone 41 M15, SilCare® Silicone 41 M20, SilCare® Silicone 41 M30 (Clariant), alkyltrimethicones SilCare® 31M30, SilCare® 31 M40, SilCare® 31M 50, SilCare® 31 M 60 (Clariant), phenyltrimethicones SilCare® 15M30, SilCare® 15M40, SilCare®15M50, SilCare® 15M60 (Clariant), polyalkylarylsiloxanes and polyethersiloxane copolymers.

The compositions according to the invention can comprise the abovementioned silicone compounds preferably in the amounts by weight of from 0.1 to 20% by weight, particularly preferably 0.2 to 15% by weight, especially preferably 0.5 to 10% by weight, based on the finished compositions.

Suitable carrier materials are preferably vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivatives.

Fungicidal active ingredients which may be used are preferably ketoconazole, oxiconazole, terbinafin, bifonazole, butoconazole, cloconazole, clotrimazole, econazole, enilconazole, fenticonazole, isoconazole, miconazole, sulconazole, tioconazole fluconazole, itraconazole, terconazole and naftifine, Zn pyrethione and octopirox in the amounts by weight of from 0.05 to 5% by weight, preferably 0.1 to 3% by weight, particularly preferably 0.2 to 2% by weight, based on the finished compositions.

The compositions according to the invention can advantageously be mixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances.

As pearlescence-imparting compounds, preference is given to fatty acid monoalkanolamides, fatty acid dialkanolamides, monoesters or diesters of alkylene glycol, in particular of ethylene glycol and/or propylene glycol or oligomers thereof with higher fatty acids, e.g. palmitic acid, stearic acid or behenic acid or mixtures thereof, monoesters or diesters of alkylene glycols with fatty acids, fatty acids and metal salts thereof, monoesters or polyesters of glycerol with carboxylic acids and ketosulfones of various types. In the compositions according to the invention, the pearlescence-imparting component is particularly preferably ethylene glycol distearate and polyethylene glycol distearate with 3 glycol units.

The moisturizing substances available are preferably isopropyl palmitate, glycerol and/or sorbitol, which are preferably used in the amounts by weight of from 0.1 to 50%.

Superfatting agents which may be used are preferably lanolin and lecithin, nonethoxylated and polyethoxylated or acylated lanolin and lecithin derivatives, polyol fatty acid esters, mono-, di- and triglycerides and/or fatty acid alkanolamides.

Suitable preservatives are preferably phenoxyethanol, parabens, pentanediol or sorbic acid. They are preferably used in the amounts by weight of from 0.001 to 5% by weight, particularly preferably from 0.01 to 3% by weight, especially preferably from 0.1 to 2% by weight, based on the finished compositions.

Dyes which can be used are the substances approved and suitable for cosmetic and pharmaceutical purposes.

Fragrance and/or perfume oils which may be used are individual odorant compounds, e.g. the synthetic products of the ester, ether, aldehyde, ketone, alcohol and hydrocarbon type. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cycllamen aldehyde, hydroxycitronellal, lilial and bourgeonal, and the ketones include, for example, the ionones, alpha-isomethylionone and methyl cedryl ketone, and the alcohols include anethole, citronellol, eugenol, geraniol, linaloyl, phenylethyl alcohol and terpineol, and the hydrocarbons include primarily the terpenes and balsams. Preference is given to using mixtures of different odorants which together produce a pleasant scent note.

Perfume oils can also comprise natural odorant mixtures, as are accessible from vegetable or animal sources, e.g. pine, citrus, jasmine, lily, rose or ylang ylang oil. Essential oils of lower volatility, which are mostly used as aroma components, are also suitable as perfume oils, e.g. sage oil, camomile oil, clove oil, melissa oil, mint oil, cinnamon leaf oil, linden blossom oil, juniper berry oil, vetiver oil, olibanum oil, galbanum oil and ladanum oil.

The acids or alkali for adjusting the pH which are used are preferably mineral acids, for example HCl, inorganic bases, for example NaOH, KOH and organic acids, preferably citric acid.

The compositions are preferably adjusted to a pH in the range from 2 to 12, preferably pH 3 to 8.

The cosmetic and pharmaceutical compositions according to the invention can be prepared using the substituted aminopolyorganosiloxanes ($S_H$).

The present invention therefore also provides the use of one or more substituted aminopolyorganosiloxanes ($S_H$) for preparing a cosmetic or pharmaceutical composition.

In a further preferred embodiment of the invention, a concentrate comprising 70 to 99.99% by weight, particularly preferably 70 to 99% by weight and especially preferably 75 to 95% by weight of one or more substituted aminopolyorganosiloxanes ($S_H$), based on the finished concentrate, is used for preparing the cosmetic or pharmaceutical compositions according to the invention.

The examples and applications below are intended to illustrate the invention in more detail without, however, limiting it thereto (all of the percentages given are percentages by weight).

EXAMPLE 1

Preparation of SilCare® Silicone SEA 951.76 parts of octamethylcyclotetrasiloxane and 38.31 parts of [N-(2-aminoethyl)-3-aminopropyl]methyldimethoxysilane are admixed with 0.95 parts of tetrabutylammonium hydroxide (40% strength methanolic solution) and heated at 70° C. under a gentle stream of nitrogen over the course of 90 minutes. After 2 hours at 70° C., the system is evacuated to a residual pressure of 50 mbar and then heated to 110° C. at a constant residual pressure. After one hour at 110° C. and 50 mbar, the mixture is cooled to room temperature under reduced pressure. Excess octamethylcyclotetrasiloxane is distilled off, and about 965.00 parts of aminomodified polydimethylsiloxane (S) with an amine number of about 0.385 are obtained.

193.00 parts of (S) are mixed, with stirring and under nitrogen, with 87.00 parts of alkyl polyglycol glycidyl ether (H), heated to 150° C. and stirred for about 8 hours at 150° C. until the conversion of (H) is complete. The reaction product is cooled and isolated. This gives 280.00 parts of silicone oil ($S_H$).

280.00 parts of silicone oil ($S_H$) are mixed, at room temperature, with 28.00 parts of tridecanol poly-9,5-glycol ether and 14 parts of water. This gives 322.00 parts of SilCare® Silicone SEA in the form of a transparent, viscous liquid which can easily be diluted further with water and has a pH of about 9.0.

EXAMPLE 2

Color Protection Application Example

Standardized, blonde-bleached hair tresses were colored using a standard commercial permanent hair color (viva pure red, fiery red) under standard conditions. The tress A was then washed with ether sulfate:betaine (3:1, 12% Al), and the tress B was washed with ether sulfate:betaine (3:1, 12% Al)+SilCare® Silicone SEA (1% Al) 4 times in each case. In the panel comprising 10 people, the tress A is set at standard (O). An improvement compared with the standard is evaluated with + or ++(very good), and a deterioration with − or −−.

The parameters of color intensity, color brilliance, shine, feel and electrostatic charging after the four washing operations are listed below (average from all of the test persons).

|  | Color intensity | Color brilliance | Shine | Feel | Electrostatic charging |
|---|---|---|---|---|---|
| Tress A (standard) | 0 | 0 | 0 | 0 | 0 |
| Tress B | + | ++ | ++ | + | 0 |

Result:

The hair tresses treated with SilCare® Silicone SEA have significantly lower bleeding of the hair color according to the visual and sensory test (increased color intensity, higher color brilliance) and additionally display a significantly improved shine and a better feel.

EXAMPLE 3

W/O Cream

| | | | |
|---|---|---|---|
| A | Hostacerin ® DGI | Clariant | 4.00% |
| | Beeswax | | 2.00% |
| | Lunacera ® M | | 3.00% |
| | Magnesium stearate | | 1.00% |
| | Mineral oil, low viscosity | | 5.00% |
| | Vaseline | | 10.00% |
| | Cetiol ® V | | 5.00 |
| | SilCare ® Silicone SEA | | 1.00% |
| B | 1,2-Propylene glycol | | 3.00% |
| | Water | | ad 100% |
| | Preservative | | q.s. |
| C | Fragrance | | 0.40% |

| Preparation method: | |
|---|---|
| I | Melting of A at 80° C. |
| II | Heating of B to 80° C. |
| III | Stirring of II into I |
| IV | Stirring until a temperature of 35° C. is reached |
| V | Addition of C to IV at 35° C. |

EXAMPLE 4

O/W Cream

| | | | |
|---|---|---|---|
| A | Hostacerin ® DGI | Clariant | 2.00% |
| | Isopropyl palmitate | | 4.00% |
| | Octyldodecanol | | 4.00% |
| | NIPAGUARD ® PDU | Clariant | q.s. |
| | SilCare ® Silicone SEA | Clariant | 1.00% |
| B | ARISTOFLEX ® AVC | Clariant | 1.20% |
| C | Hostapon ® KCG | Clariant | 0.80% |
| | Water | | ad 100% |
| D | Fragrance | | 0.40% |

| Preparation method: | |
|---|---|
| I | Stirring of B into A |
| II | Stirring of D into I |
| III | Homogenization |

EXAMPLE 5

Moisture Cream Gel

| | | | |
|---|---|---|---|
| A | Mineral oil, low viscosity | | 7.00% |
| | SilCare ® 15 M50 | Clariant | 5.00% |
| B | Aristoflex ® AVC | Clariant | 1.00% |
| C | Water | | ad 100% |
| | Glycerol | | 8.00% |
| | SilCare ® Silicone SEA | Clariant | 1.00% |
| | Preservative | | q.s. |
| D | Fragrance | | 0.30% |

| Preparation method: | |
|---|---|
| I | Mixing of A and B |
| II | Stirring of C into I, then addition of D |
| III | Homogenization |

EXAMPLE 6

Skincare Oil

| A | SilCare ® Silicone 31M50 | Clariant | 40.00% |
|---|---|---|---|
|   | SilCare ® Silicone 41M15 | Clariant | 20.00% |
|   | Cyprylic/Capric Triglyceride |   | 38.60% |
|   | SilCare ® Silicone SEA | Clariant | 1.00% |
|   | SilCare ® Silicone 1M75 | Clariant | 0.40% |

Preparation method:

| I | Mixing of components A |
|---|---|

EXAMPLE 7

Cream Rinse

| A | Hostacerin ® DGI | Clariant | 1.50% |
|---|---|---|---|
|   | Cetyl alcohol |   | 3.00% |
| B | Genamin ® CTAC | Clariant | 3.30% |
|   | Water |   | ad 100% |
|   | Preservative |   | q.s. |
| C | Fragrance |   | 0.30% |
|   | SilCare ® Silicone SEA | Clariant | 1.00% |

Preparation method:

| I | Melting of A at about 75° C. |
|---|---|
| II | Heating of B to about 75° C. |
| III | Addition of II to I with stirring and further stirring until 30° C. |
| IV | Addition of C to III at 30° C. |
| V | Adjustment to pH 4.0 with citric acid |

EXAMPLE 8

Hair Shampoo

| A | Genapol ® LRO liquid | Clariant | 31.10% |
|---|---|---|---|
|   | Fragrance |   | 0.30% |
| B | Water |   | ad 100% |
|   | SilCare ® Silicone SEA | Clariant | 1.00% |
|   | Genagen ® CAB | Clariant | 12.00% |
|   | Fragrance |   | q.s. |
|   | Preservative |   | q.s. |
| C | NaCl |   | 6.00% |

Preparation method:

| I | Mixing of components A |
|---|---|
| II | Successive addition of the components B to I |
| III | Adjustment of the pH |
| IV | Adjustment of the viscosity using C |

EXAMPLE 9

Shampoo with Color Protection for Colored Hair

| A | Glucamat DOE-120 |   | 2.00% |
|---|---|---|---|
|   | Emulsogen ® HCO 040 | Clariant | 2.00% |
| B | Water |   | ad 100% |
| C | Genapol ® LRO liquid | Clariant | 22.22% |
|   | Genagen ® KB | Clariant | 13.33% |
|   | Genamin ® KSL | Clariant | 3.33% |
|   | Aristoflex ® PEA 70 | Clariant | 2.86% |
|   | Sandopan ® DTC, acid | Clariant | 2.20% |
|   | NIGAGUARD ® DCB | Clariant | 0.10% |
|   | SilCare ® Silicone SEA | Clariant | 0.50% |
|   | Dye |   | q.s. |
|   | Fragrance |   | 0.20% |
| D | NaOH |   |   |

Preparation method:

| I | Stirring of components A into B and heating to about 60° C. and with stirring Cooling to room temperature |
|---|---|
| II | Successive stirring of components C into I |
| III | Stirring until the formulation appears clear |
| IV | Adjustment to pH 5.5 with D |

EXAMPLE 10

Tinting Shampoo

| A | Genagen ® KB | Clariant | 7.00% |
|---|---|---|---|
|   | Velsol semipermanent dye | Clariant | 0.50% |
| B | Genapol ® T 500 P | Clariant | 0.50% |
|   | Water |   | ad 100% |
| C | Genapol ® LRO liquid | Clariant | 30.00% |
|   | Genagen ® LAA | Clariant | 3.00% |
|   | Genamin ® CTAC | Clariant | 1.00% |
|   | SilCare ® Silicone SEA | Clariant | 0.50% |
|   | Tetrasodium EDTA |   | 0.10% |
|   | NIGAGUARD ® DMDMH | Clariant | 0.30% |
|   | Genapol ® PDB | Clariant | 3.00% |
|   | Potassium phosphate |   | 1.50% |
| D | Citric acid |   |   |

Preparation method:

| I | Dissolution of the components with stirring |
|---|---|
| II | Mixing of components B and heating until the solution is clear |
| III | Cooling of B to about 35° C. and subsequent addition of the components C to II |
| IV | Stirring of I into III |
| V | Adjustment to pH 5.5 with D |

EXAMPLE 11

Hair Gel

| A | Aristoflex ® AVC | Clariant | 1.40% |
|---|---|---|---|
|   | Water |   | ad 100% |
| B | Diaformer Z-751 |   | 3.00% |
|   | Alcohol denat. |   | 30.00% |
|   | Genapol ® C100 | Clariant | 0.40% |
|   | Fragrance |   | 0.20% |
| C | Dye |   | q.s. |
|   | Phenonip ® | Clariant | 0.50% |
| D | SilCare ® Silicone SEA | Clariant | 0.50% |

Preparation method:

| I | Dissolution of components A |
|---|---|
| II | Mixing of components B |
| III | Addition of II to I with stirring |
| IV | Addition of C to III |
| V | Addition of D to IV |

EXAMPLE 12

Hair Ends Care

| A | Water | | 50.0% |
|---|---|---|---|
| B | Tylose ® H 100000 G4 | | 1.00% |
| C | Water | | ad 100% |
| D | Genamin ® PDAC | Clariant | 2.50% |
|   | Glycerol | | 2.00% |
|   | SilCare ® Silicone SEA | Clariant | 1.00% |
| E | Citric acid | | q.s. |

Preparation method:

| I | Swell B in A |
|---|---|
| II | Successive dissolution of the individual components of D in C |
| III | Addition of II to I |
| IV | Adjustment of the pH with E |

EXAMPLE 13

Antiperspirant

| A | Locron ® L | Clariant | 10.00% |
|---|---|---|---|
|   | Ethanol | | 50.00% |
|   | Farnesol | | 0.50% |
|   | Fragrance | | 0.20% |
|   | Water | | ad 100% |
|   | Extrapon Avocado special | | 0.50% |
|   | SilCare ® Silicone SEA | Clariant | 1.00% |

Preparation method:

Mixing of components A

EXAMPLE 14

Deodorant

| A | Octopirox ® | Clariant | 0.30% |
|---|---|---|---|
| B | Ethanol | Clariant | 70.00% |
| C | Perfume | | 0.50% |
|   | Softigen ® 767 | | 0.50% |
| D | Allantoin | Clariant | 0.10% |
|   | SilCare ® Silicone SEA | Clariant | 1.00% |
| E | Water | | ad 100% |
| F | Citric acid | | q.s. |

Preparation method:

| I | Mixing of A and B |
|---|---|
| II | Addition of C to I |
| III | Dissolution of D in warm E, addition of II |
| IV | Adjustment of the pH with F |

EXAMPLE 15

Antiacne Gel

| A | Octopirox ® | Clariant | 0.10% |
|---|---|---|---|
| B | Ethanol | Clariant | 25.00% |
|   | Propylene glycol | | 20.00% |
| C | Perfume | | 0.20% |
|   | NIPAGUARD ® CMB | Clariant | 0.10% |
| D | Aristoflex ® HMB | Clariant | 1.30% |
| E | Allantoin | Clariant | 0.10% |
|   | SilCare ® Silicone SEA | Clariant | 1.00% |
| F | Water | | ad 100% |

Preparation method:

| I | Dissolution of A in B |
|---|---|
| II | Addition of C to I |
| III | Stirring of D into II |
| IV | Dissolution of E in heated water |
| V | Addition of IV to III with stirring |

Chemical name of the commercial products used

| Aristoflex ® AVC | (Clariant) | Ammonium acryloyldimethyltaurate/ NVP copolymer (NVP: N-vinylpyrrolidone) |
|---|---|---|
| Aristoflex ® HMB | (Clariant) | Ammonium acryloyldimethyltaurate/ beheneth-25 methacrylate polymer |
| Aristoflex ® PEA 70 | (Clariant) | Polypropylene terephthalate |
| Cetiol ® V | (Cognis) | Decyl oleate |
| Diaformer Z-751 | | Lauryl/stearyl acrylate, ethyleneamine oxide, methacrylate copolymer |
| Emulsogen ® HCO 040 | (Clariant) | PEG-40 hydrogenated castor oil |
| Extrapon Avocado special | | Water/ethoxydiglycol/propylene glycol/butylene glycol/*persea gratissima* extract |
| Genagen ® CAB | (Clariant) | Cocoamidopropylbetaine |
| Genagen ® KB | (Clariant) | Cocobetaine |
| Genagen ® LAA | (Clariant) | Sodium lauroamphoacetate |
| Genamin ® CTAC | (Clariant) | Cetrimonium chloride |
| Genamin ® KSL | (Clariant) | PEG-5 stearylammonium lactate |
| Genamin ® PDAC | (Clariant) | Polyquaternium-6 |
| Genapol ® C100 | (Clariant) | Coceth-10 |
| Genapol ® PDB | (Clariant) | Glycol distearate/laureth-4/ cocoamidopropylbetaine |
| Genapol ® LRO fl. | (Clariant) | Sodium laureth sulfate |
| Genapol ® T 500 P | (Clariant) | Ceteareth-50 |
| Glucamat DOE-120 | | PEG-120 methylglusose dioleate |
| Hostacerin ® DGI | (Clariant) | Polyglyceryl-2 sesquiisostearate |
| Hostapon ® KCG | (Clariant) | Sodium cocoylglutamate |
| Locron ® L | (Clariant) | Aluminum chlorohydrate |
| Lunacera ® M | (H. B. Fuller) | Microcrystalline wax |
| NIPAGUARD ® CMB | (Clariant) | Triethylene glycol/benzyl alcohol/ propylene glycol/ chloromethylisothiazolinone/ methylisothiazolinone |
| NIPAGUARD DCB | (Clariant) | Phenoxyethanol, methyldibromo- glutaronitrile |
| NIGAGUARD ® DMDMH | (Clariant) | DMDM hydantoin |
| NIPAGUARD ® PDU | (Clariant) | Propylene glycol/diazolidinyl urea/ methylparaben/propylparaben |
| Octopirox ® | (Clariant) | Piroctone olamine |
| Phenonip ® | (Clariant) | Phenoxyethanol/methyl-/ethyl-/ butyl-/propyl-/isobutylparaben |
| Sandopan ® DTC, Säure | (Clariant) | Trideceth-7 carboxylic acid |
| SilCare ® 1M75 | (Clariant) | Retinoxytrimethylsilane |
| SilCare ® 15M50 | (Clariant) | Phenyltrimethicone |
| SilCare ® 31M50 | (Clariant) | Caprylyltrimethicone |
| SilCare ® 41M15 | (Clariant) | Caprylylmethicone |
| SilCare ® Silicone SEA | (Clariant) | Example 1 |
| Softigen ® 767 | (Sasol) | PEG-6 caprylic/capric glyceride |
| Tylose ® H 100000 G4 | | Hydroxyethylcellulose |

The invention claimed is:

1. A method for protecting and preserving color in colored keratin fibers, wherein the method comprises the step of contacting the colored keratin fibers with a treatment composition comprising at least one substituted aminopolyorganosiloxanes ($S_H$) with substituted amino groups which are bonded to silicon atoms of a polysiloxane basic structure via alkylene bridges or mono- or oligo(alkylenamino)alkylene bridges, where the amino groups present in the aminopolyorganosiloxanes ($S_H$) are substituted at least partially by a radical of the formula (ε)

$$T-CH_2-CHOH-CH_2- \quad (\epsilon),$$

in which T is the radical of a surfactant monoalcohol polyglycol ether with emulsifier character, wherein the monoalcohol polyglycol ether is of the following formula (II)

$$R_1-(O-X)_q-OH \quad (II)$$

in which $R_1$ is an alkylaromatic or aliphatic hydrocarbon radical having 9 to 24 carbon atoms, X is a C2-4 alkylene and q is 4 to 50, where at least 80% of the q alkylenoxy groups are ethylenoxy units, the amino groups present in the aminopolyorganosiloxanes ($S_H$) being substituted in the average ratio of at least 1.5 radicals of the formula (ε) per Si-bonded aminoalkyl group or amino-mono- or -oligo-(alkylenamino)-alkyl group and optionally present amino groups can be acylated, alkylated, benzylated and/or protonated at least partially.

2. The method of claim 1, wherein the treatment composition comprises from 0.01 to 10% by weight of the at least one substituted aminopolyorganosiloxanes ($S_H$), based on the treatment composition.

3. The method of claim 1, wherein the colored keratin fibers are colored human hair.

4. The method of claim 1, wherein the substituted aminopolyorganosiloxane ($S_H$) has an average molecular weight in the range from 15 000 to 2 000 000.

5. The method of claim 1, wherein the aminopolyorganosiloxane ($S_H$) has an amine number in the range from 0.05 to 3.

6. The method of claim 1, wherein the substituted aminopolyorgano-siloxane ($S_H$) has been obtained by reaction of at least one aminopolyorganosiloxane (s) which comprises primary and/or secondary amino groups which are bonded to silicon atoms of the polysiloxane basic structure via alkylene bridges or mono- or oligo(alkylenamino)alkylene bridges, with at least one alcohol polyglycol ether monoglycidyl ether (H) and, optionally, a subsequent step selected from the group consisting of acylation, alkylation, benzylation, protonation, and mixtures thereof.

7. The method as claimed in claim 1, wherein the substituted aminopolyorganosiloxane ($S_H$) has a nitrogen content in the range from 0.03 to 4.2% by weight.

8. The method as claimed in claim 1, wherein all of the amino groups of the substituted aminopolyorganosiloxane ($S_H$) are 40 to 100% substituted by radicals of the formula (ε).

* * * * *